United States Patent
Salmisuo

(10) Patent No.: US 9,629,936 B2
(45) Date of Patent: Apr. 25, 2017

(54) METHOD AND DEVICE FOR GENERATING STEAM AND GASEOUS HYDROGEN PEROXIDE

(71) Applicant: STERIS EUROPE, INC. SUOMEN SIVULIIKE, Tuusula (FI)

(72) Inventor: Mauri Salmisuo, Tuusula (FI)

(73) Assignee: STERIS EUROPE, INC. SUOMEN SIVULIIKE, Tuusula (FI)

( * ) Notice: Subject to any disclaimer, the term of this patent is extended or adjusted under 35 U.S.C. 154(b) by 0 days.

(21) Appl. No.: 14/726,890

(22) Filed: Jun. 1, 2015

(65) Prior Publication Data

US 2015/0343107 A1    Dec. 3, 2015

(30) Foreign Application Priority Data

Jun. 3, 2014   (EP) .................... 14397517

(51) Int. Cl.
*A61L 2/20* (2006.01)
*A61L 2/07* (2006.01)
(Continued)

(52) U.S. Cl.
CPC ............ *A61L 2/208* (2013.01); *A61L 2/00* (2013.01); *A61L 2/07* (2013.01); *A61L 9/00* (2013.01);
(Continued)

(58) Field of Classification Search
CPC ... A61L 2/208; A61L 2/07; A61L 9/00; A61L 2/00; F22B 1/284; F22B 1/28; C01B 15/01; B01B 1/005
See application file for complete search history.

(56) References Cited

U.S. PATENT DOCUMENTS

| | | |
|---|---|---|
| 1,585,671 A | 5/1926 | Harms |
| 2,281,906 A | 5/1942 | Adams |

(Continued)

FOREIGN PATENT DOCUMENTS

| | | | |
|---|---|---|---|
| EP | 2286846 A1 | 2/2011 | |
| JP | 11076372 A | * 3/1999 | ............... A61L 2/06 |

(Continued)

OTHER PUBLICATIONS

European Search Report issued in corresponding European Patent Application No. 15397525, dated Oct. 21, 2015.

(Continued)

*Primary Examiner* — Regina M Yoo
(74) *Attorney, Agent, or Firm* — Kusner & Jaffe; Michael A. Centanni

(57) ABSTRACT

Vaporized hydrogen peroxide is used for decontamination of enclosed and sealed areas. It is capable of destroying all forms of microbial life. It is commonly produced from a solution of liquid $H_2O_2$ and water, by means of generators specifically designed for the purpose. The present invention provides a combined source for heating steam and vaporized hydrogen peroxide and a method for simultaneously supplying steam and vaporized hydrogen peroxide. A device according to the invention comprises a chamber adapted for receiving water through an inlet and expelling steam through an outlet. A vessel for receiving and vaporizing hydrogen peroxide solution is provided in close contact with the chamber. Heat from the water vapor in the chamber is allowed to supply the required energy for producing hydrogen peroxide vapor in the vessel from an aqueous solution.

8 Claims, 2 Drawing Sheets

(51) Int. Cl.
   *B01B 1/00*      (2006.01)
   *C01B 15/01*     (2006.01)
   *F22B 1/28*      (2006.01)
   *A61L 2/00*      (2006.01)
   *A61L 9/00*      (2006.01)
(52) U.S. Cl.
   CPC .............. *B01B 1/005* (2013.01); *C01B 15/01* (2013.01); *F22B 1/28* (2013.01); *F22B 1/284* (2013.01); *A61L 2202/11* (2013.01)

(56) References Cited

U.S. PATENT DOCUMENTS

| | | | |
|---|---|---|---|
| 2,467,492 A | 4/1949 | Olson | |
| 2,472,362 A | 6/1949 | Barnebey et al. | |
| 4,637,916 A * | 1/1987 | Hennebert | A61L 2/204 422/27 |
| 5,258,162 A | 11/1993 | Andersson et al. | |
| 5,443,802 A * | 8/1995 | Freedman | A61L 2/07 422/111 |
| 5,997,827 A | 12/1999 | Mezger et al. | |
| 6,406,666 B1 | 6/2002 | Cicha et al. | 422/28 |
| 6,884,392 B2 * | 4/2005 | Malkin | A61B 1/123 134/198 |
| 7,258,062 B2 * | 8/2007 | Green | A47J 43/12 99/293 |
| 8,372,169 B2 * | 2/2013 | Tsangaris | C10J 3/20 48/120 |
| 2004/0172877 A1 * | 9/2004 | Wunning | B01B 1/005 48/102 A |
| 2006/0272956 A1 * | 12/2006 | Felder | C12M 21/04 205/637 |
| 2010/0099173 A1 * | 4/2010 | Ko | A61L 2/14 435/287.1 |
| 2013/0236357 A1 * | 9/2013 | Tremblay | A61L 2/202 422/33 |
| 2014/0023558 A1 * | 1/2014 | Erickson | A01N 25/06 422/128 |

FOREIGN PATENT DOCUMENTS

| | | | | |
|---|---|---|---|---|
| JP | 2006271585 A | * | 10/2006 | ............. A61H 33/10 |
| WO | WO 2007/003313 A1 | | 1/2007 | |
| WO | WO 2011/076400 A1 | | 6/2011 | |

OTHER PUBLICATIONS

Search report issued in corresponding European Patent Application No. 14397517.5, dated Nov. 13, 2014.
Examiner's Requisition issued in corresponding Canadian Patent Application No. 2,893,397 dated Sep. 21, 2016.

* cited by examiner ent Application No. 14397517.5, filed Jun. 3, 2014, the entire
METHOD AND DEVICE FOR GENERATING STEAM AND GASEOUS HYDROGEN PEROXIDE

RELATED APPLICATION

This application claims the benefit of European Patent Application No. 14397517.5, filed Jun. 3, 2014, the entire content of which is hereby incorporated by reference.

FIELD OF THE INVENTION

The invention relates to the field of sterilization using hydrogen peroxide in vapor or gaseous form. More particularly, the invention relates to a method and device for generating hydrogen peroxide vapor in combination with the generation of steam, which is commonly required for sterilization purposes.

BACKGROUND OF THE INVENTION

Vaporized hydrogen peroxide (VHP®) is used for decontamination of enclosed and sealed areas. It is capable of destroying all forms of microbial life, including bacteria, bacterial spores, fungi, fungal spores, and viruses. It is commonly produced from a solution of liquid $H_2O_2$ and water, by means of generators specifically designed for the purpose. Aqueous hydrogen peroxide may be supplied as a 35% stabilized solution, for example Vaprox® supplied by Steris Corporation.

For producing hydrogen peroxide vapor, several methods have been developed and suggested. In WO2007003313 is disclosed the impingement of a spray of hydrogen peroxide solution on a heat transfer surface to generate gaseous agent. This has been said to cause buildup of impurities on the heat transfer surface. According to U.S. Pat. No. 5,258,162, a spray of hydrogen peroxide solution may instead be introduced in a heated carrier gas stream which conveys the energy required for atomization. In EP 2 286 846 is disclosed how the atomization may be effected using ultrasound. In WO2011076400, a flash evaporator is disclosed having a series of wells in a heating block, into which wells hydrogen peroxide solution can be individually fed. A gas stream in a flow channel above the wells carries the total vaporized material from the series of wells to the point of use. In U.S. Pat. No. 5,997,827 is disclosed a device having a porous tube section which hydrogen peroxide solution penetrates, vaporizing into a heated air stream flowing to a feed tube. The vaporizing section and the feed tube are steam heated.

In this context, "steam" refers to water in gaseous or condensing form. "Vacuum" refers to a pressure below atmospheric.

Certain products, e.g. products containing heat-sensitive biological material in aqueous solution or in dry form, require sterilization at relatively moderate temperatures due to the thermal sensitivity of the materials involved. Proteins, steroids and vaccine components are examples. In such cases, the use of vacuum, steam and hydrogen peroxide vapor is often an adequate solution. By means of pressure control, the temperature of the steam and the hydrogen peroxide vapor can be adjusted to a desired level. A lower pressure corresponds to a lower temperature in the steam and the hydrogen peroxide vapor.

An apparatus for sterilization using a closed space in which goods are treated with hydrogen peroxide vapor requires, in addition to a source of hydrogen peroxide, a source of steam for heating the enclosure to which the load is confined to the maximum temperature allowed.

SUMMARY OF THE INVENTION

The present invention provides a combined source for heating steam and vaporized hydrogen peroxide. Also the carrier gas for the hydrogen peroxide may be brought to the correct temperature by means of a unit according to the invention.

The primary source of heat can be an electrical heating coil, or tubing containing a circuit with heat transfer medium as the skilled person may contemplate. According to a first aspect, a device according to the invention comprises a chamber adapted for receiving water through an inlet and expelling steam through an outlet, and a primary heat source associated with the chamber; preferably, this is the single heat source involved. A vessel for receiving and vaporizing hydrogen peroxide solution (in the following denoted the vessel) is provided in close contact with the chamber, although not communicating with it in the sense of allowing fluid transfer. Heat from the water vapor in the chamber is allowed to supply the required energy for producing hydrogen peroxide vapor in the vessel from an aqueous solution. The hydrogen peroxide vessel is integrated with the chamber so that at least part of the outer wall of the vessel forms part of the inner walls delimiting the chamber, whereby heat transfer occurs readily across the whole of the surface separating the interior of the chamber from the interior of the vessel. The vessel is embedded in the chamber so that the vessel is situated wholly in the steam space, i.e. above the water level during operation. Means are provided for preventing contact of the liquid water with the vessel. For example, one or more water level switches may be provided to control the water feed, to ensure that direct liquid water contact with the vessel outer surface does not occur. The level monitoring may be implemented by any technical means known to the skilled person, e.g. by floats, optical or capacitive sensors, or by an overflow arrangement. This arrangement ensures that the vaporization surface for hydrogen peroxide solution inside the vessel never reaches a temperature above that of steam at the pressure in the chamber.

Preferably, the surface mentioned above through which heat transfer occurs (the heat transfer surface) is dimensioned to transfer heat corresponding to at least 1/10 of the total heating effect of the primary heat source. Preferably, the heat transfer surface corresponds to 1/10 to 1/5 of the total heating effect of the primary heat source. More preferably, the heat transfer surface corresponds to about 1/10 of the total heating effect of the primary heat source.

The capacity requirement for the primary heat source is determined by the size of the space used for sterilization in an apparatus served by the combined source for heating steam and vaporized hydrogen peroxide, and the pressure used. A space formed by a vacuum grade chamber of 2-4 $m^3$ requires an effect of about 15 kW. For example, a 3 $m^3$ chamber may be served by a primary heat source of 15 kW, whereby the heat transfer capacity of the heat transfer surface is 1500 W. The capacity of the heat transfer surface is determined by material parameters. For example, stainless steel of 1 mm thickness has a heat transfer capacity of about 90 $kW/m^2$.

The chamber is provided with an inlet for feed water and an outlet for steam, as well as an appropriate connection or connections for controlling the internal pressure of the chamber, i.e. a line connected to a vacuum source. Connections for temperature and pressure sensors and level control instrumentation are provided as required.

A closed conduit for carrier gas for vaporized hydrogen peroxide may pass through the chamber. This provides for bringing the carrier gas to the correct equilibrium temperature before it is conducted to the hydrogen peroxide vessel. The conduit ends in a nozzle within the vessel, in which is also provided an outlet for transporting vaporized hydrogen peroxide to the goods to be sterilized. A device designed according to the principles set out above has the capacity to generate a hydrogen peroxide concentration of at least 2 mg/l in the load space of a connected sterilization apparatus.

The vessel for receiving hydrogen peroxide solution is arranged in close contact with the chamber so that heat transfer from the water vapor in the chamber occurs evenly over the whole heat transfer surface of the vessel. Advantageously, the vessel is embedded in the chamber so as to form an integral part of the chamber structure.

The operating pressure of the device according to the invention may be in the range 1 mbar-1000 mbar; the operating temperature may be in the range 20-120° C., all depending on the requirements of the sterilization schedule.

According to a further aspect of the invention, a method is provided for supplying steam and vaporized hydrogen peroxide to a sterilization apparatus using a single heat source, comprising the generation of steam within a first, essentially closed space using a heat source; conducting at least part of the generated steam to the sterilization apparatus; providing for heat transfer from the steam across a wall of said first essentially closed space to a second essentially closed space; conducting hydrogen peroxide solution into said second space to generate vaporized hydrogen peroxide by means of said transferred heat; and conducting vaporized hydrogen peroxide from the second space to the sterilization apparatus. Preferably a carrier gas is conducted into said second space to facilitate the transfer of the vaporized hydrogen peroxide to the sterilization apparatus. Preferably, the carrier gas is preheated by conducting it in a closed conduit through the first space whereby it exchanges heat with the steam in the first space, and preferably the preheating leads to thermal equilibrium between the carrier gas and the steam.

"Essentially closed space" in this context means that fluid transfer to and from the spaces occurs only via connections provided for these purposes.

BRIEF DESCRIPTION OF THE DRAWINGS

The invention is described in further detail in the following with reference to the attached drawings, in which.

DETAILED DESCRIPTION OF THE PREFERRED EMBODIMENTS

Figure 1:
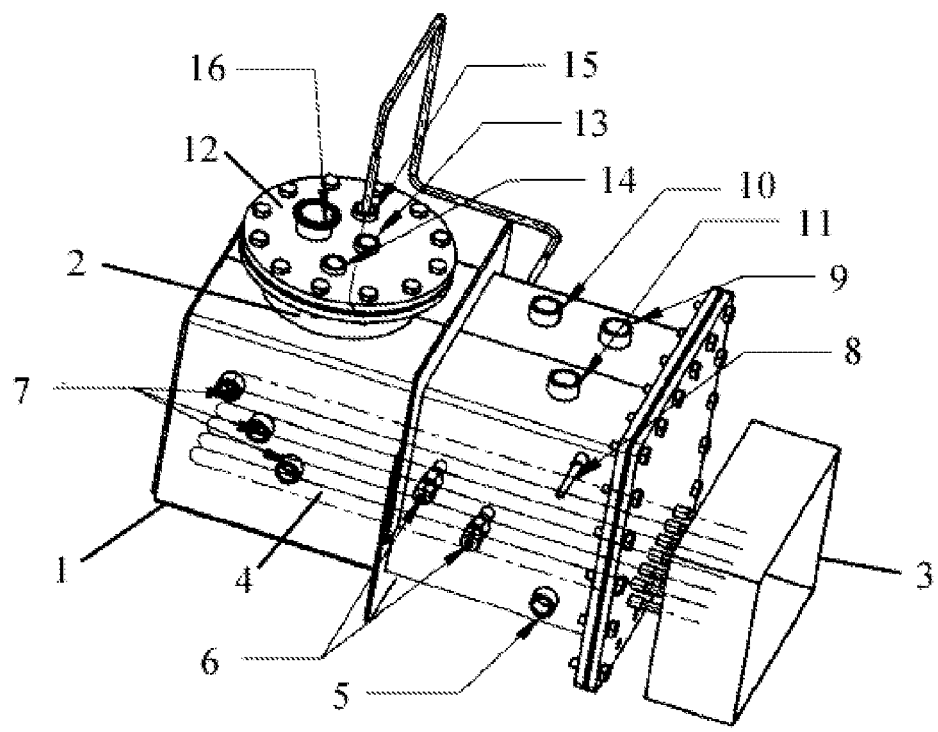
FIG. 1 is a perspective drawing of a device according to the invention

In FIG. 1 is shown a device in accordance with the invention for the simultaneous generation of steam and hydrogen peroxide vapor. In the upper wall of chamber 1, which here has the shape of a box, is provided an embedded vessel 2, here in the shape of a cylinder. The chamber is equipped with a heating unit which in the embodiment shown is an electrical unit 3 having heating coils 4 extending into the chamber near its bottom wall.

In the chamber, several inlets and outlets are provided. In the side wall which is visible in FIG. 1 are water inlet 5, temperature probe connections 6 and water level switch connections 7. Further, carrier gas inlet 8 is shown. Some or all of these connections could be provided in the opposite side wall of the chamber if required.

In the top wall of the chamber are vacuum connection 9, steam outlet 10 and vacuum transmitter connection 11.

In the lid 12 of hydrogen peroxide vessel 2 are provided several in- and outlet connections.

Through inlet 13, hydrogen peroxide solution is fed into the vessel. The vessel internal pressure is adjusted through connection 14, connected to a vacuum line as described below. Carrier gas enters the vessel through inlet 15, and the hydrogen peroxide vapor is led out via outlet 16.

Figure 2:
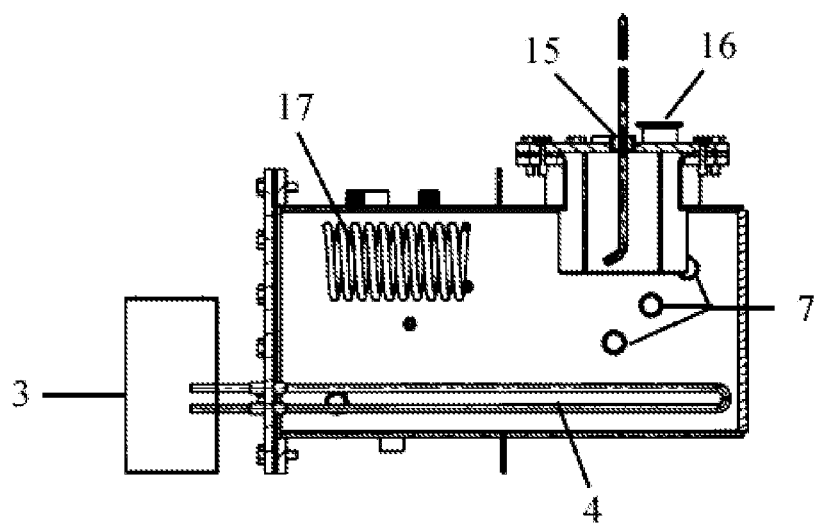
FIG. 2 is a sectional side view of a device according to the invention

Several of these features are also shown in FIG. 2, in which the carrier gas conduit, in this embodiment in the form of a spiral coil 17, is visible.

During operation, feed water is supplied through inlet 5. It is heated by means of primary heat supplied by heating coils 4 to a temperature corresponding to its boiling temperature at the pressure determined by the vacuum generated within the chamber via connection 14. The source of primary heat is electricity in the embodiment shown, but the primary heat may be supplied in any manner known to the skilled person, e.g. steam or a heat transfer medium. The water level is kept at a level below the bottom of hydrogen peroxide vessel 2, the level being controlled by level switches connected at 7. The upper half of the chamber thus is a steam space held at the temperature required for the sterilization task at hand.

From this steam space, heating steam is conducted to a sterilization device as described below in connection with FIG. 3. Within the steam space is the carrier gas conduit in the form of spiral coil 17. The length of the conduit is dimensioned according to the required flow of carrier gas to allow the gas stream to reach thermal equilibrium with the chamber before it enters the hydrogen peroxide vessel.

During operation, the hydrogen peroxide vessel is also in thermal equilibrium with the steam chamber, which supplies sufficient heat to produce the required flow of vaporized hydrogen peroxide. The hydrogen peroxide is dosed into the vessel through inlet 13, preferably not allowing any stagnant liquid to form in the vessel. The dosing may be carried out using a dosing pump from a storage flask.

Figure 3:
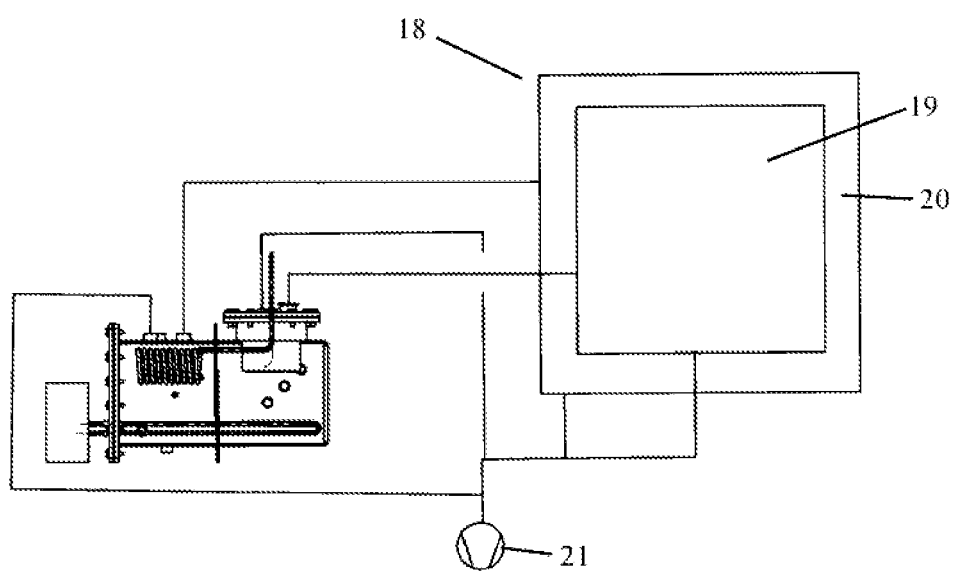
FIG. 3 is a schematic drawing of a device according to the invention connected to a jacketed chamber for sterilizing heat sensitive articles.

FIG. 3 shows the device of the invention as in FIG. 2 schematically connected to a sterilization device 18, having an inner enclosure 19 for containing a load for sterilization and a jacket 20 for thermal control. The enclosure and the jacket are both connected to a vacuum source 21. Appropriate tubing also connects the vacuum source to the steam chamber and the hydrogen peroxide vessel. Control and shut-off valves for controlling the pressure in the various components of the apparatus are naturally provided as the skilled person can contemplate, but these have been omitted for clarity in the schematic FIG. 3.

The whole apparatus being under computer control, it can be adapted for sterilization cycles according to the requirements of the relevant articles.

In the embodiment shown, the hydrogen peroxide vessel is a cylindrical body embedded in the upper wall of a box-shaped chamber for generating steam. The walls or the bottom of the vessel, or both, may be smooth or have a structure that extends the heat transfer area. Other shapes and other relative dimensions are possible as long as proper heat transfer is secured for keeping the hydrogen peroxide vessel in thermal equilibrium with the steam chamber during operation as well as a favorable flow route for the carrier gas and vaporized hydrogen peroxide.

Having described the invention, the following is claimed:

1. A device for simultaneous generation of steam and vaporized hydrogen peroxide, said device comprising:
    a chamber having an inlet for receiving water, an associated heat source for generating steam from the received water, and an outlet for conducting the generated steam out of the chamber;
    a vessel in contact with and extending through an upper wall of the chamber, the vessel having an inlet through which a hydrogen peroxide solution is received, a vessel wall across which heat from the generated steam is conducted to vaporize the received hydrogen peroxide solution into vaporized hydrogen peroxide, and an outlet for conducting the vaporized hydrogen peroxide out of the vessel; and
    one or more water level switches configured to inhibit contact between the received water and the vessel wall.

2. The device according to claim 1, wherein the vessel is a cylinder embedded in the chamber.

3. The device according to claim 1, further comprising a carrier gas conduit adapted to pass through the chamber and ending in a nozzle within the vessel.

4. The device according to claim 3, wherein the carrier gas conduit is in the form of a spiral coil.

5. A method for supplying steam and vaporized hydrogen peroxide to a sterilization apparatus using a single heat source, comprising the generation of steam within a first essentially closed space; conducting at least part of said steam to the sterilization apparatus; providing for heat transfer from the steam across a wall of said first essentially closed space to a second essentially closed space; conducting hydrogen peroxide solution into said second essentially closed space to generate vaporized hydrogen peroxide by using said transferred heat, and conducting the vaporized hydrogen peroxide to the sterilization apparatus.

6. The method according to claim 5, further comprising conducting a carrier gas into the second essentially closed space to facilitate transfer of the hydrogen peroxide to the sterilization apparatus.

7. The method according to claim 6, further comprising bringing the carrier gas into heat exchange with the first essentially closed space.

8. The method according to claim 7, comprising thermally equilibrating the carrier gas in the second essentially closed space with the steam in the first essentially closed space.

* * * * *